United States Patent
Nakashima et al.

(10) Patent No.: US 10,231,989 B2
(45) Date of Patent: Mar. 19, 2019

(54) RENAL INSUFFICIENCY PROGRESSION INHIBITOR, PROPHYLACTIC AGENT FOR RENAL INSUFFICIENCY AND INDOXYL SULFATE PRODUCTION INHIBITOR

(71) Applicant: euglena Co., Ltd., Shiba (JP)

(72) Inventors: Ayaka Nakashima, Yokohama (JP); Yuta Asayama, Yokohama (JP); Osamu Iwata, Yokohama (JP); Kengo Suzuki, Yokohama (JP)

(73) Assignee: Euglena Co., Ltd., Minato-ku, Tokyo (JP)

( * ) Notice: Subject to any disclaimer, the term of this patent is extended or adjusted under 35 U.S.C. 154(b) by 0 days.

(21) Appl. No.: 15/514,966

(22) PCT Filed: Sep. 29, 2015

(86) PCT No.: PCT/JP2015/077523
§ 371 (c)(1),
(2) Date: Mar. 28, 2017

(87) PCT Pub. No.: WO2016/052509
PCT Pub. Date: Apr. 7, 2016

(65) Prior Publication Data
US 2017/0224717 A1    Aug. 10, 2017

(30) Foreign Application Priority Data

Sep. 29, 2014   (JP) ................. 2014-199433

(51) Int. Cl.
*A61K 31/716*   (2006.01)
(52) U.S. Cl.
CPC .................. *A61K 31/716* (2013.01)
(58) Field of Classification Search
None
See application file for complete search history.

(56) References Cited

U.S. PATENT DOCUMENTS

| 2003/0203016 A1 | 10/2003 | Suwelack et al. |
| 2004/0197352 A1 | 10/2004 | Ranganathan |
| 2012/0329752 A1 | 12/2012 | Suzuki |

FOREIGN PATENT DOCUMENTS

| IT | LU940013 A1 | 5/1996 |
| JP | 2003529538 A | 10/2003 |
| JP | 2006273772 A | 10/2006 |
| JP | 2007507526 A | 3/2007 |
| JP | 2010095460 A | 4/2010 |
| JP | 2014024817 A | 2/2014 |
| WO | 2011111707 A1 | 9/2011 |

OTHER PUBLICATIONS

Sugiyama, J. Vet. Med. Sci. 71(7): 885-890, 2009.*
Coonnbes, Kidney International (2012) 81, 233-236.*
Hsu, Kidney International (2008) 74, 101-107.*
International Preliminary Report on Patentability and Translation of Written Opinion, dated Dec. 8, 2015, from the International Bureau in counterpart International application No. PCT/JP2015/077523.
Tanaka, et al., "Studies on Implantation of Bifidobacterium", Japan J. Pediatr., vol. 33, 2483 (1980), 11 pages.
Niwa, "Chronic Renal Failure Treatment Focusing on Progression Factor", The Current Medicine, vol. 47, No. 1: 55-61 (1999), 8 pages.
Bayrak et al., "Oral β-Glucan Protects Kidney against Ischemia/Reperfusion Injury in Rats", American Journal of Nephrology, 2008, vol. 28, No. 2, pp. 190-196, Oct. 24, 2007 (7 pages total).
FDA GRAS Notice (GRN) No. 513, Euglena gracilis, "Containing β-1,3-Glucan for Use as a Human Food Supplement", (retrieved on Apr. 12, 2017),Feb. 13, 2014 (71 pages total).
Barsanti et al., "Chemistry, physico-chemistry and applications linked to biological activities of β-glucans", The Royal Society of Chemistry, Nat. Prod. Rep., Dec. 31, 2011, vol. 28, pp. 457-466 (10 pages total).
Written Opinion, dated Dec. 15, 2017, issued by the Intellectual Property Office of Singapore in counterpart application No. 11201702354T.

* cited by examiner

*Primary Examiner* — Layla D Berry
(74) *Attorney, Agent, or Firm* — Sughrue Mion, PLLC

(57) ABSTRACT

Provided are a novel renal failure progression inhibitor, prophylactic agent for renal failure, and indoxyl sulfate production inhibitor, intended for human use, in particular, for a patient with renal failure. The renal failure progression inhibitor, prophylactic agent for renal failure, and indoxyl sulfate production inhibitor each comprises paramylon derived from *Euglena* or a processed product thereof as an active ingredient. In the case of the renal failure progression inhibitor, for example, paramylon is continuously orally administered to a patient suffering from chronic renal failure, undergoing a dialysis therapy, several times per day in a dose of 1 to 5 g per intake. In particular, the renal failure progression inhibitor is singly administered to the patient in a capsule or powdered preparation at a prescribed time interval before and after administration of other drugs.

2 Claims, 9 Drawing Sheets

RENAL INSUFFICIENCY PROGRESSION INHIBITOR, PROPHYLACTIC AGENT FOR RENAL INSUFFICIENCY AND INDOXYL SULFATE PRODUCTION INHIBITOR

CROSS REFERENCE TO RELATED APPLICATIONS

This application is a National Stage of International Application No. PCT/JP2015/077523, filed Sep. 29, 2015, claiming priority based on Japanese Patent Application No. 2014-199433, filed Sep. 29, 2014, the contents of all of which are incorporated herein by reference in their entirety.

Technical Field

The present invention relates to a novel renal failure progression inhibitor, prophylactic agent for renal failure and indoxyl sulfate production inhibitor.

Background Art

There are currently about 300,000 or more patients with end stage renal failure in Japan and the number of the patients goes on increasing. A fundamental therapeutic method is not available for end stage renal failure and major renal replacement therapies include a hemodialysis, a peritoneal dialysis, and a kidney transplant. However, any of these replacement therapies put a large burden on the patients. Thus, it is important to suppress the progression of renal failure during an early phase of symptoms and an effective renal failure progression inhibitor and a therapeutic agent for renal failure have been desired.

It is commonly known that the patients with renal failure have in their bodies increased levels of the blood concentration of indoxyl sulfate, which is a uremic substance serving as a progressive factor of renal failure and an angiopathy risk factor, the blood concentration of creatinine indicative of renal dysfunction, the blood concentration of homocysteine, which is a risk factor of a cardiovascular disease caused by atherosclerosis, and neutral fat.

Of these, in particular, indoxyl sulfate has been reported (see Non patent literature 1) to be a genuine uremia substance serving as a progressive factor of renal failure and the blood concentration of indoxyl sulfate in the patients with chronic renal failure is abnormally higher than the blood concentration of indoxyl sulfate of healthy persons.

Since indoxyl sulfate is a substance that facilities the progression of renal failure and deteriorates its symptoms as described above, it is believed that lowering the blood concentration of indoxyl sulfate of the patients with renal failure can significantly alleviate obstacles to a renal function and suppress the progression of renal failure. On the other hand, indoxyl sulfate is an extremely troublesome metabolic product, which cannot be removed even by the renal replacement therapies described above.

Regarding this point, it has been known that a spherical adsorptive carbon as a conventional renal failure progression inhibitor absorbs indole, a precursor of indoxyl sulfate, in the intestine and excretes indole in the feces, thereby enabling to reduce the blood concentration of indoxyl sulfate. As a result, according to the report, the progression of renal failure is suppressed and the mortality rate caused by a cardiovascular disease is also reduced due to the suppression of the onset of the cardiovascular disease associated with renal failure.

However, prescription of the spherical adsorptive carbon as an internal medicine places a burden on the patients for reasons such as that they need to take 30 capsules a day. Moreover, administration of the spherical adsorptive carbon causes a severe side effect such as abdominal distension and constipation resulting in extreme suffering when used for a long period. As such, it frequently happens that the patients ask to stop the prescription of the spherical adsorptive carbon.

Therefore, there is a demand for a new drug, which works with a lower dose and reduces the pains and burdens of the patients by not causing abdominal distension and constipation or the like.

As a potential new drug, for example, a prophylactic and therapeutic agents for chronic renal failure containing chitosan known as an adsorbent have been proposed (see Patent literature 1).

Specifically, it is reported that, in the results of animal experiment studies using a renal failure model rat, an oral administration agent containing chitosan as an active ingredient can lower the blood concentration of indoxyl sulfate, which is a uremia substance as well as a causing substance for an oxidative stress environment.

However, a result of clinical trials targeting human, in particular, a patient with chronic renal failure, has not been reported, and verifications have been needed regarding efficiency and safety to the patients and further studies have been needed regarding dosage and administration, such as an administration period, an administration procedure, and an administration amount in order to reduce the pains and burdens of the patients.

On the other hand, *Euglena* (generic name: *Euglena*, Japanese name: Midorimushi) is attracting attention as a promising biological resource to be used as a food, a feed, a fuel, and the like.

*Euglena* contains 59 kinds of nutrients, such as vitamins, minerals, amino acids, and unsaturated fatty acids, which correspond to a majority of nutrients that are necessary for humans to maintain life, and it has been proposed that *Euglena* can be used as a supplement for taking a variety of nutrients in a well-balanced manner and as a food supply source in an impoverished region where people cannot take in necessary nutrients.

It has been difficult to perform a mass culture of *Euglena* for the reasons including that *Euglena* is predated by a predator as it is positioned at the lowest bottom of the food chain and that setting culture conditions, such as a light and temperature conditions and a shaking speed, is difficult as compared with other microorganisms. However, extensive studies conducted by the present inventors have recently established a mass culture technique and opened the door to a large supply of *Euglena* and paramylon extracted from *Euglena*.

*Euglena* is a unique organism in that it has an animal-like feature with flagellum movement while it also contains chloroplast to perform photosynthesis like a plant. Thus, it has been expected that *Euglena* itself and a substance derived from *Euglena* have many functions.

Therefore, it is desirable to elucidate a function and a mechanism of exerting the function of *Euglena* and a substance derived from *Euglena* such as paramylon, which now can be supplied in large quantities, and then to develop a method and the like for utilizing these materials.

CITATION LIST

Patent Literature

Patent Literature 1: JP 2014-24817 A

Non Patent Literature

Non Patent Literature 1: Toshimitsu Niwa, The Current Medicine Volume 47, Number 1: 55-61 (1999)
Non Patent Literature 2: Tanaka, R. et al.: Jpn. J. Pediatr., 33, 2483 (1980)

SUMMARY OF INVENTION

Technical Problem

The present invention has been made in view of the above-mentioned problems and an object of the present invention is to provide a novel renal failure progression inhibitor, prophylactic agent for renal failure, and indoxyl sulfate production inhibitor for a living body.

Another object of the present invention is to provide a renal failure progression inhibitor, a prophylactic agent for renal failure, and an indoxyl sulfate production inhibitor, capable of lowering the blood concentration of indoxyl sulfate, which is hardly removed even by a dialysis therapy, in a body of human, in particular, a patient with renal failure.

Another object of the present invention is to provide a renal failure progression inhibitor, a prophylactic agent for renal failure and, an indoxyl sulfate production inhibitor, as a novel method for utilizing a substance derived from *Euglena*.

Solution to Problem

The present inventors studied intensively and found that administering paramylon derived from *Euglena* to a living body can lower the blood concentration of indoxyl sulfate, which is a uremic substance.

Specifically, indole, a precursor of indoxyl sulfate, is a putrefaction product produced by intestinal bad bacteria decomposing tryptophan abundantly contained in proteins of the diet. In view of the above, the present inventors found that, upon administration of paramylon or a processed product of paramylon to human, in particular, a patient with renal failure, paramylon exerts an effect of adsorbing indole and lowers the blood concentration of indoxyl sulfate, thereby completing the present invention.

Further, it is generally known that, in the intestinal tract of a patient undergoing a hemodialysis therapy for renal failure, the number of intestinal bad bacteria, such as *Escherichia coli*, increases while the number of good anaerobic bacteria, such as bifidobacteria and lactic acid bacteria, decreases. Further, the intestinal bacterial flora can be improved by ingesting bifidobacteria, lactic acid bacteria, and the like (Non patent literature 2).

Regarding the above, the present inventors have intensively studied and found that paramylon derived from *Euglena* can contribute to the improvement of an intestinal environment in human. Specifically, the present invention has been completed upon a finding that administering paramylon derived from *Euglena* to a living body decreases the number of intestinal bad bacteria and increases the number of bifidobacteria and lactic acid bacteria in the intestine.

Further, the present inventors studied intensively and found that administering paramylon derived from *Euglena* to a living body reduces intestinal transit time of the orally ingested diet as a synergistic effect that is not exhibited by a conventional spherical adsorptive carbon, and thus suppresses the production amount of indole produced by the decomposition of tryptophan in the intestine, thereby completing the present invention.

Therefore, the above-described problems can be solved by the renal failure progression inhibitor of the present invention, comprising paramylon or a processed product thereof as an active ingredient.

According to the above configuration, the blood concentration of indoxyl sulfate can be reduced by paramylon upon administration of paramylon or the processed product thereof to the patient with renal failure. Thus, the present invention can be used as a progression inhibitor for renal failure.

In one aspect, administration may be performed to a patient suffering from renal failure and undergoing a dialysis therapy.

According to the above configuration, while indoxyl sulfate is a uremic substance generally hardly removed even by a dialysis therapy, administration of paramylon to the patient undergoing the dialysis therapy can reduce the blood concentration of indoxyl sulfate of the patient and prevent the further progression and deterioration of, for example, end stage renal failure.

In one aspect, administration may be performed to a patient suffering from chronic renal failure and being between the ages of 50 and 70.

According to the above configuration, considering that the average age of patients with end stage renal failure at the time of starting the dialysis therapy in general is 68.4 years (Overview of Regular Dialysis Treatment in Japan, as of Dec. 31, 2012, The Japanese Society for Dialysis Therapy), administration of paramylon to a patient between the ages of 50 and 70, at a stage prior to starting the dialysis therapy, can prevent the progression of renal failure of the patient at a stage prior to starting the dialysis therapy.

In one aspect, the paramylon or the processed product thereof may be continuously administered to a patient suffering from chronic renal failure three times per day in a dose of 1 to 5 g per intake.

Further, oral administration may be performed to the patient suffering from chronic renal failure in a capsule or powdered preparation.

Further, administration may be performed singly to the patient suffering from chronic renal failure at a prescribed time interval before and after administration of other drug.

According to the above configuration, the renal failure progression inhibitor containing the paramylon or the processed product thereof as an active ingredient can be provided to the patient with renal failure after determining dosage and administration, such as an administration period, an administration procedure, and an administration amount, where an effect of the paramylon is high.

Further, a prophylactic agent for renal failure, a therapeutic agent for uremia, an indoxyl sulfate production inhibitor, or a prophylactic agent for a cardiovascular disease, comprising the paramylon or the processed product thereof as an active ingredient, can be realized.

Further, a food for specified health uses for suppressing the progression of renal failure, comprising the paramylon or the processed product thereof as an active ingredient, can be realized.

Further, a method for suppressing the progression of renal failure, comprising the administration of a composition containing the paramylon or the processed product thereof as an active ingredient, can be realized (excluding medical practice for human).

In addition, a method for suppressing the progression of renal failure, comprising the administration or ingestion of the paramylon or the processed product thereof in an effective amount to a living body (human), in particular, a patient, can be realized.

Further, the paramylon or the processed product thereof can be used in the production of a therapeutic agent for suppressing the progression of renal failure.

Further, the renal failure progression inhibitor, characterized by being the paramylon or the processed product thereof, can be applied to the production of a therapeutic agent for suppressing the progression of renal failure.

Effects of Invention

According to the present invention, a novel renal failure progression inhibitor, prophylactic agent for renal failure and, indoxyl sulfate production inhibitor for a living body can be provided.

Further, a renal failure progression inhibitor, a prophylactic agent for renal failure, and an indoxyl sulfate production inhibitor, capable of lowering the blood concentration of indoxyl sulfate hardly removed even by a dialysis therapy in a body of human, in particular, a patient with renal failure, can be provided.

Further, a renal failure progression inhibitor, a prophylactic agent for renal failure, and an indoxyl sulfate production inhibitor, as a novel method for utilizing a substance derived from *Euglena*, can be provided.

DESCRIPTION OF EMBODIMENTS

Figure 1:
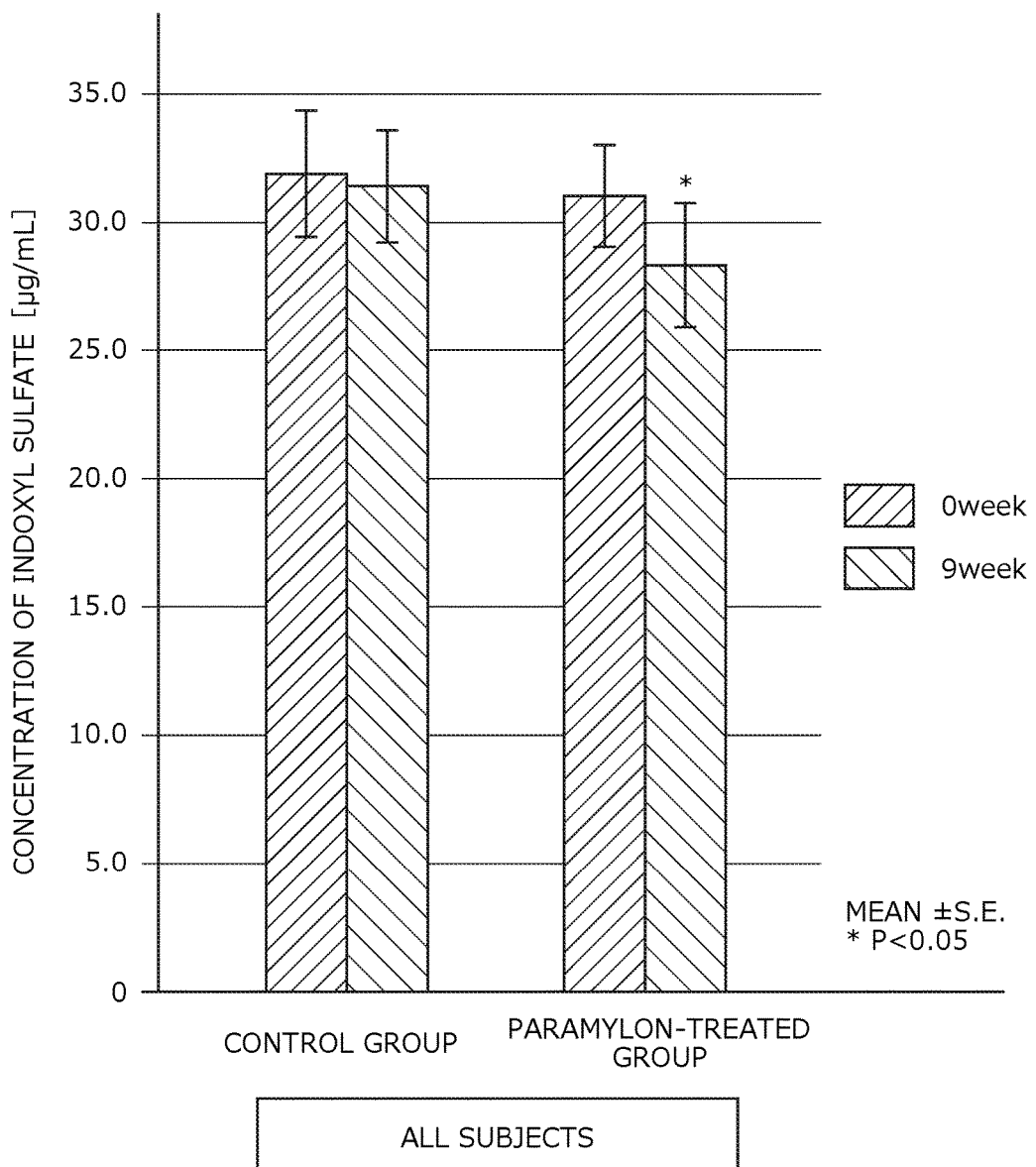
FIG. 1 is a graph illustrating an amount of change of the blood concentration of indoxyl sulfate in a patient with renal failure, who receives a renal failure progression inhibitor of this example for 9 weeks.

Embodiments of the present invention will be described below with reference to FIG. 1 to FIG. 9.

The present embodiments relate to the invention of a renal failure progression inhibitor comprising paramylon derived from *Euglena* or a processed product thereof as a main ingredient, the renal failure progression inhibitor being administered to a patient with renal failure to lower the blood concentration of indoxyl sulfate in a living body and suppress the progression and deterioration of renal failure.

<Overview of Renal Failure>

"Renal failure" refers to a condition in which a renal function is decreased to about 30% or less compared to that in the normal state. Renal failure is classified into acute renal failure, which presents a rapidly progressive loss of the renal function, and chronic renal failure, which presents a gradual loss of the renal function over a long period of time.

First, the acute renal failure causes, as a result of the rapid loss of the renal function, an increase in the blood concentration of creatinine (e.g., an increase by 0.5 mg/dL or more per day), an increase in the blood concentration of urea nitrogen (e.g., an increase by 10 mg/dL or more per day), abnormalities in the concentrations of water and an electrolyte in the body fluid, and the like, thereby leading to a condition in which homeostasis of the body fluid cannot be maintained.

The acute renal failure is classified into prerenal, intrinsic renal, and postrenal, depending on an area where it starts.

The prerenal acute renal failure is a pathological condition in which the renal blood flow and the glomerular filtration rate are reduced due to exacerbation of the blood circulation dynamics and the main causes of the prerenal acute renal failure include heart failure, myocardial infarction, external pericarditis, vasculitis, arteriosclerosis, bilateral renal artery stenosis, activation of the renin-angiotensin system, sepsis, anaphylaxis, liver cirrhosis, anesthetic, bleeding, dehydration, vomiting, diarrhea, edema, ascites accumulation, burn, nephrotic syndrome, adrenal failure, and the like.

The intrinsic renal acute renal failure is a pathological condition caused by dysfunction of glomerulus, renal tubule, and interstitium of the kidney and the main causes of the intrinsic renal acute renal failure include acute glomerulonephritis, connective tissue disease, hemolytic-uremic syndrome, acute tubular necrosis, hypercalcaemia, drug allergy, pyelonephritis, NSAIDs, narrow sense of acute tubular necrosis progressed from prerenal state, antibiotics, contrast medium, heavy metal, multiple myeloma, hyperuricemia, rhabdomyolysis, DIC, and the like.

The postrenal acute renal failure is a pathological condition caused by obstruction of urinary tract and the main causes of the postrenal acute renal failure include urinary tract obstruction (stones, tumors, and retroperitoneal fibrosis), benign prostatic hyperplasia, tumor, stones, and the like.

In general, the acute renal failure needs a dialysis therapy and is healed through an initiating phase, an oliguric phase, a diuretic phase, and a recovery phase in this order by a successful dialysis therapy. On the other hand, in a serious form of acute renal failure, the renal function may not recover and the treatment may be moved to a continuous dialysis therapy.

Although the mortality rate during the diagnosis of the acute renal failure has declined by advances of the dialysis therapy, it is still about 50% and thus the acute renal failure is considered as a dangerous disease among renal diseases.

Next, the chronic renal failure is a pathological condition in which the renal function is irreversibly decreased by various chronic, progressive renal diseases and exhibits various clinical conditions, such as hypertension and anemia with abnormal bone metabolism, due to failure to maintain homeostasis of the body fluid. In particular, various clinical symptoms appeared in end stage renal failure are called uremia, and a treatment of uremia requires blood purification by the dialysis therapy.

A progression degree of the chronic renal failure is generally classified from stage 1 to stage 5 according to a classification of chronic kidney disease (CKD)(Clinical Practice Guidebook for Diagnosis and Treatment of Chronic Kidney Disease 2012, The Japanese Journal of Nephrology 2012).

Chronic kidney disease (CKD) is diagnosed by a urine protein and a glomerular filtration rate ((GFR), ml/min/1.73 $m^2$) in routine clinical practice and evaluated with estimated GRF (eGFR) calculated with the blood concentration of creatinine (Cr) based on age and gender using Japanese equation for estimating GFR in a routine diagnosis.

It is noted that the glomerular filtration rate (GFR) is an index for measuring the renal function (capacity of the kidney to excrete body wastes into urine) and the value becomes lower with reduction in the renal function.

In the stage 1 of CKD, the GFR value is in the normal range (GFR≥90) although kidney damage is present. In the stage 2, kidney damage is present with the GFR value slightly lower than normal (GFR=60 to 89). In those stages, there is still remaining renal function with almost no symptoms.

In the stage 3 of CKD, kidney damage is present with the medium GFR value (GFR=30 to 59). In this stage, the size of remaining renal function becomes incomplete, thereby causing an increase in the amount of urine and the blood concentration of urea nitrogen, and mild anemia. As a result, it becomes difficult to maintain homeostasis of the body fluid.

In the stage 4 of CKD, kidney damage is present with the high GFR value (GFR=15 to 29). In this stage, the symptoms in the stage 3 are exacerbated. It is noted that CKD in the stages 1 to 4 is called conservative stage renal failure, representing a condition prior to starting the dialysis therapy.

Finally, in the stage 5 of CKD, end stage renal failure is developed and the dialysis therapy becomes necessary (GFR<15). In this stage, uremic symptoms become apparent with the progression of abnormality in the body fluid.

Examples of major causative diseases of the chronic renal failure include diabetic nephropathy, chronic nephritis (chronic glomerulonephritis), nephrosclerosis, and the like.

Development of the end stage renal failure causes an exceedingly high mortality risk without performing the dialysis therapy that alternates the renal function or a kidney transplant. In general, a recommended criterion for initiation of the dialysis therapy is referred to be the blood concentration of creatinine of 8 mg/dl or more or the blood concentration of urea nitrogen of 100 mg/dl or more.

It is noted that the dialysis therapy is a therapeutic method for artificially purifying the blood by dialysis when body wastes cannot be removed due to renal failure and uremia, and mainly classified into two types, namely hemodialysis and peritoneal dialysis.

Further, the dialysis therapy includes a specialized type of the dialysis therapy such as hemofiltration excellent in removing middle molecular weight materials as compared to hemodialysis, hemodiafiltration, which is obtained by a combination of hemodialysis and hemofiltration and is excellent in removing a wide range of materials from low molecular weight materials to low molecular weight protein materials, continuous hemodiafiltration, which is slowly performed for a prolonged time in patients who cannot bear hemodialysis due to a low cardiac function, as well as blood adsorption for removing a specific material using an absorbent, and plasma exchange for separating and removing the plasma from the blood and returning new plasma and the like to the blood.

<Overview of Indoxyl Sulfate>

Next, a description is given of indoxyl sulfate, which is a uremic substance found in high concentration in the blood of a patient with renal failure and serves as a progressive factor of renal failure.

Indoxyl sulfate is a metabolic product of proteins in the diet. Specifically, indole, a precursor of indoxyl sulfate, is produced by the decomposition of tryptophan contained in proteins by intestinal bad bacteria such as *Escherichia coli*. Indole is then absorbed in the digestive tract and subjected to sulfuric acid conjugation in the liver to produce indoxyl sulfate.

Indoxyl sulfate is released to the blood, predominantly bound to albumin, and mainly excreted from kidney into urine without being metabolized. However, indoxyl sulfate is accumulated in high concentration in the blood of the patient with renal failure due to reduced renal function.

Indoxyl sulfate is known to be involved in fibrosis, glomerular hardening, and the like in the kidney, cause induction of active oxygen and reduction of radical scavengers, induce a cardiovascular disease, and facilitate the progression and deterioration of renal failure.

Further, the blood concentration of indoxyl sulfate in a living body is known to correlate with the blood concentration of creatinine and the blood concentration of urea nitrogen, serving as an index for measuring the renal function. Thus, it is considered that reducing the blood concentration of indoxyl sulfate would remarkably alleviate renal dysfunction associated with renal failure.

Therefore, it is considered that reducing the blood concentration of indoxyl sulfate in the living body of the patient with renal failure would lead to suppression of the progression of renal failure.

<Renal Failure Progression Inhibitor>

Paramylon or a processed product thereof as a main ingredient of the renal failure progression inhibitor includes paramylon extracted from *Euglena* cells, paramylon powders, a variety of paramylon processed products, and the like.

As *Euglena* cells, *Euglena gracilis* (*E. gracilis*), in particular, *Euglena gracilis* (*E. gracilis*) Z strain is preferably used. Besides, species such as *Euglena gracilis* Klebs and *Euglena gracilis* var. *bacillaris*, an SM-ZK strain as amutant strain (chloroplast-deficient strain) derived from the *Euglena gracilis* (*E. gracilis*) Z strain and var. *bacillaris* as a variant of *Euglena gracilis*, β-1,3-glucanase derived from a gene mutation strain, such as a chloroplast-defective mutant strain of these species, *Euglena intermedia*, *Euglena piride*, and other *Euglena* species such as *Astaia longa* may be used.

*Euglena* is widely distributed in fresh water such as a pond and a marsh and *Euglena* obtained from these places may be used. Alternatively, any *Euglena* that is already isolated may be used.

*Euglena* according to the present invention includes any mutant strains of *Euglena*. Further, these mutant strains include any strains obtained by a genetic method, such as, for example, recombination, transduction, and transformation.

For culturing *Euglena* cells, a culture medium to which nutrient salts such as a nitrogen source, a phosphorus source, and a mineral are added, for example, a modified Cramer-Myers culture medium (($NH_4$)$_2HPO_4$ 1.0 g/L, $KH_2PO_4$ 1.0 g/L, $MgSO_4$-$7H_2O$ 0.2 g/L, $CaCl_2$-$2H_2O$ 0.02 g/L, $Fe_2(SO_2)_3$-$7H_2O$ 3 mg/L, $MnCl_2$-$4H_2O$ 1.8 mg/L, $CoSO_4$-$7H_2O$ 1.5 mg/L, $ZnSO_4$-$7H_2O$ 0.4 mg/L, $Na_2MoO_4$-$2H_2O$ 0.2 mg/L, $CuSO_4$-$5H_2O$ 0.02 g/L, thiamin hydrochloride (vitamin $B_1$) 0.1 mg/L, and cyanocobalamin (vitamin $B_{12}$) (pH3.5)) may be used. It is noted that any of ($NH_4$)$_2SO_4$ and $NH_3$aq may be used instead of ($NH_4$)$_2HPO_4$. Further, known Hutner medium and Koren-Hutner medium prepared based on the description of *Euglena*-physiology and biochemistry (Shozaburo Kitaoka ed, Gakkai Shuppan Center) may be used.

The medium has pH of preferably 2 or higher and the upper limit of pH is preferably 6 or lower, more preferably 4.5 or lower. Adjusting the pH on an acidic side allows a photosynthetic microorganism to more predominantly grow than other microorganisms, thereby enabling to suppress contamination.

Further, the culture of *Euglena* cells can be performed by, for example, a fed-batch culture method, however any liquid culture methods including flask culture and culture using a fermenter, repeated batch culture method, semi-batch culture method (fed-batch culture method), continuous culture method (perfusion culture method), and the like, may be used.

Separation of *Euglena* cells is performed by, for example, centrifugation or simple sedimentation of the culture medium.

Paramylon has a porous polymer body (β-1,3-glucan) produced by polymerization of approximately 700 glucoses through β-1,3-bonds and is contained in *Euglena* as a storage polysaccharide. A paramylon particle is in a flat and spheroidal shape and is formed by spirally tangling β-1,3-glucan chains.

The paramylon particle is isolated from cultured *Euglena* cells by any suitable method, purified into a fine particulate state, and then provided commonly as a powder.

For example, the paramylon particle can be obtained by (1) culturing *Euglena* cells in any suitable medium; (2) separating *Euglena* cells from the medium; (3) isolating paramylon from the separated *Euglena* cells; (4) purifying the isolated paramylon; and optionally (5) cooling and subsequently freeze drying the purified paramylon.

Isolation of paramylon is performed, for example, by using non-ionic or anionic surfactant, which causes mostly biodegradation. Purification of paramylon is performed substantially simultaneously with isolation.

It is noted that isolation and purification of paramylon from *Euglena* are well known and described, for example, in E. Ziegler, "Die naturlichen and kunstlichen Aromen" Heidelberg, Germany, 1982, Chapter 4.3 "Gefriertrocken", DE 43 28 329 or JP 2003-529538 T.

Examples of the processed product of paramylon include amorphous paramylon.

Amorphous paramylon is a substance obtained by amorphosizing crystalline paramylon derived from *Euglena*.

Amorphous paramylon has a relative crystallinity of 1 to 20% with respect to crystalline paramylon produced from *Euglena* by a well-known method.

It is noted that the relative crystallinity was determined by a method described in Japanese Patent Application No. 2010-52042.

Specifically, amorphous paramylon and paramylon are each pulverized by a pulverizer (ball mill MM400 manufactured by Retsch Co. Ltd.) with a frequency of 20 times/sec for 5 min and subjected to scan in a range of $2\theta=5°$ to $2\theta=30°$ under the conditions of a tube voltage of 45 KV and a tube current of 40 mA using an X-Ray diffractometer (H'PertPRO manufactured by Spectris Co., Ltd.) to obtain diffraction peaks Pc and Pa of paramylon and amorphous paramylon, respectively, at around $2\theta=20°$.

The relative crystallinity of amorphous paramylon is calculated by applying the values of Pc and Pa to a formula, relative crystallinity of amorphous paramylon=Pa/Pc×100 (%).

Amorphous paramylon is prepared according to a method described in Japanese Patent Application No. 2010-52042, in which crystalline paramylon powders are subjected to an alkali treatment, neutralized with an acid, washed, dewatered, and dried.

Examples of other processed products of paramylon include water-soluble paramylon, sulfated paramylon, and other paramylon derivatives, obtained by subjecting paramylon to a chemical or physical treatment using various known methods.

<Inhibitory Effect of Renal Failure Progression>

Paramylon or a processed product thereof, contained in the renal failure progression inhibitor, can lower the blood concentration of the indoxyl sulfate when administered to a patient with renal failure.

Details of the mechanism of action are described as follows.

(1) Paramylon or the processed product thereof serving as an main active ingredient of the renal failure progression inhibitor has a porous shape and directly absorbs indole, a precursor of indoxyl sulfate, in the intestine of the patient with renal failure.

Further, paramylon or the processed product thereof is hardly digestible, thus it passes through the digestive tract while absorbing indole without being absorbed in the living body, and is excreted together with indole in the feces.

Thus, a production amount of indoxyl sulfate, produced from indole absorbed into the digestive tract and subjected to sulfuric acid conjugation in the liver, can be reduced. Since release of indoxyl sulfate into the blood is suppressed, the blood concentration of indoxyl sulfate can be reduced.

(2) Further, paramylon or the processed product thereof serving as a main active ingredient of the renal failure progression inhibitor contributes to improvement of an intestinal environment in human, which is not observed by a conventional spherical adsorptive carbon.

(2-1) Specifically, paramylon or the processed product thereof administered to a living body activates and propagates good bacteria, such as bifidobacteria and lactic acid bacteria, in human intestine. Thus, it can improve the balance of intestinal bacteria of a patient with renal failure, where, in general, the number of intestinal bad bacteria increases and the number of good bacteria decreases.

The production amount of indole, produced by intestinal bad bacteria decomposing tryptophan contained in proteins of the diet, is suppressed by suppressing the proliferation of intestinal bad bacteria, thus the production amount of indoxyl sulfate can be suppressed.

(2-2) Further, paramylon or the processed product thereof administered to a living body shortens intestinal transit time of the orally ingested diet, thereby suppressing the production amount of indole produced from tryptophan while the diet passes through the intestine. As a result, the production amount of indoxyl sulfate can be suppressed.

The mechanism of action described above allows the renal failure progression inhibitor of the present embodiment to lower the blood concentration of indoxyl sulfate upon administration to a patient with renal failure.

<<Usage>>

The renal failure progression inhibitor of the present embodiment can be used for suppressing the progression and deterioration of acute renal failure upon administration to a patient with acute renal failure.

In particular, the concentration of indoxyl sulfate in the patient with acute renal failure sometimes increases rapidly and blood vessels damaged by indoxyl sulfate cause a cardiovascular disease that might lead to death, making the effect of the renal failure progression inhibitor advantageous.

Further, the renal failure progression inhibitor can be applied to any patients with acute renal failure regardless of types of acute renal failure, i.e., prerenal, intrinsic renal, or postrenal, and regardless of phases of acute renal failure, i.e., an initiating phase, an oliguric phase, a diuretic phase, or a recovery phase.

Further, the renal failure progression inhibitor can be applied to patients suffering from the above-mentioned diseases causing acute renal failure and those at risk of these diseases, and thus can be used as a prophylactic agent for acute renal failure.

The renal failure progression inhibitor of the present embodiment can be used for suppressing the progression and deterioration of chronic renal failure upon administration to a patient with chronic renal failure.

Further, the renal failure progression inhibitor can be applied to any patients with chronic renal failure regardless of the CKD stages ranging from stages 1 to 5 and a patient who has had a kidney transplant. For example, it can also delay the introduction of dialysis to a patient with conservative stage renal failure in the CKD stages 1 to 4.

Further, the renal failure progression inhibitor can be applied to patients suffering from diabetic nephropathy, chronic nephritis (chronic glomerulonephritis), nephrosclerosis, and the like, previously described as causing diseases of chronic renal failure, and those at risk of these diseases, and thus can be used as a prophylactic agent for chronic renal failure.

The renal failure progression inhibitor of the present embodiment can be used as a composition and the like, such as a pharmaceutical composition and a food composition, containing the renal failure progression inhibitor.

(Pharmaceutical Composition)

In a pharmaceutical field, provided is a pharmaceutical composition exhibiting a renal failure progression inhibitory effect, the pharmaceutical composition being formulated by combining paramylon in an amount sufficient for effectively exhibiting effect of lowering the blood concentration of indoxyl sulfate with pharmaceutically acceptable carriers and additives. Such a pharmaceutical composition may be a pharmaceutical product or a quasi-pharmaceutical product.

In particular, the pharmaceutical composition is preferably prepared by including lactic acid bacteria, bifidobacteria, butyric acid bacteria, and the like, having a beneficial effect on an intestinal function. In this manner, the effect of the renal failure progression inhibitor is synergistically increased. Specifically, suppression of proliferation of intestinal bad bacteria, such as *Escherichia coli*, and reduction of putrefaction products produced by intestinal bad bacteria can be achieved in a synergistic manner by the beneficial effect on an intestinal function described above.

Further, the pharmaceutical composition is also preferably prepared by including a pH adjuster for lowering pH (hydrogen ion concentration exponent) in the intestine in order to suppress proliferation of intestinal bad bacteria. In this manner, the effect of the renal failure progression inhibitor is synergistically increased.

The pharmaceutical composition may be prepared for internal use or external use. Thus, the pharmaceutical composition may be used in preparation forms, which include an oral preparation, an injection preparation such as for intravenous injection, subcutaneous injection, intradermal injection, intramuscular injection, and/or intraperitoneal injection, a preparation for transmucosal administration, a preparation for transdermal administration, and the like.

A dosage form of the pharmaceutical composition may be suitably selected depending on the preparation form, and examples of the dosage form include a solid preparation such as a tablet, a granule, a capsule, a powdered preparation, and a powder, a liquid preparation such as a solution and a suspension, an ointment, and a semisolid preparation such as a gel.

(Food Composition)

In a food field, there can be provided a food composition exhibiting a renal failure progression inhibitory effect, the food composition being formulated by combining paramylon as a food material in an amount sufficient for effectively exhibiting the renal failure progression inhibitory effect in a living body with a variety of foods.

In particular, the food composition is preferably prepared as a food by including lactic acid bacteria, bifidobacteria, butyric acid bacteria, and the like, having a beneficial effect on the intestinal function, and as a food by including a pH adjuster. In this manner, the effect of the renal failure progression inhibitor is synergistically increased.

That is, the present invention can provide the food composition which can be indicated as "for help preventing renal failure progression" and the like in a food field. Examples of such a food composition include a food in general, a food for specified health uses, a food with nutrient function claims, a food with function claims, a hospital food for patient, a supplement, and the like. Further, it can be used as a food additive.

Examples of the food composition include a seasoning, a processed meat product, a processed agricultural product, a beverage (a soft drink, an alcoholic beverage, a carbonated beverage, a milk beverage, a fruit juice, a tea, a coffee, an energy drink, etc.), a powdered beverage (a powdered juice, a powdered soup, etc.), a concentrated beverage, a confectionery (a candy, a cookie, a biscuit, a gum, a gummy, a chocolate, etc.), a bread, a cereal, and the like. Further, the food for specified health uses, the food with nutrient function claims, the food with function claims, and the like, may be provided in a form of a capsule, a lozenge, a syrup, a granule, a powder, and the like.

The food for specified health uses described herein is a food containing a health function ingredient that influences a physiological function and the like of the body and approved by Secretary-General of the Consumer Affairs Agency for displaying an indication that the food is suitable for a specified health uses. The food of the present invention is expected to be marketed with an indication that it helps suppressing renal failure progression, preventing and ameliorating renal failure, preventing and ameliorating uremia, inhibiting production of indoxyl sulfate in a living body, and the like, as specified health uses.

Further, the food with nutrient function claims is a food used for supplementing a nutritional ingredient (a vitamin and a mineral) and displays an indication describing a function of the nutritional ingredient. In order to sell the food with nutrient function claims, an amount of the nutritional ingredient included in recommended consumption per day needs to be between a predetermined upper limit value and lower limit value, and it is necessary to display an alert indication and the like in addition to the nutrient function.

Further, the food with function claims is a food that displays functional effectiveness based on scientific evidence under the food business operator's own responsibility. Information and the like on the evidence supporting safety and functional effectiveness of the product are submitted to the Secretary-General of the Consumer Affairs Agency before the product is marketed.

The aforementioned present invention containing paramylon or the processed product thereof as an active ingredient can be used as a food for specified health uses for suppressing progression of renal failure, a food with nutrient function claims for suppressing progression of renal failure, and a food with function claims for suppressing progression of renal failure, intended for a patient with renal failure and an animal other than human, suffering from renal failure.

Further, the present invention containing paramylon or the processed product thereof as an active ingredient can be used as a food for specified health uses for suppressing progression of renal failure, a food with nutrient function claims for suppressing progression of renal failure, and a food with function claims for suppressing progression of renal failure, intended for a living organism, for example, human before affection to renal failure, human at risk of renal failure, and human before being diagnosed or treated with renal failure, and an animal other than human.

<<Dosage and Administration>>

The renal failure progression inhibitor of the present embodiment may be orally administered to a patient with renal failure and preferably orally administered to a patient with chronic renal failure.

The patient with chronic renal failure may be a patient undergoing a dialysis therapy, a patient before receiving a dialysis therapy, or a patient after receiving a kidney transplant. Administration is more preferably performed to a patient with chronic renal failure, undergoing the dialysis therapy. Administration is further preferably performed to a male patient with chronic renal failure between the ages of 50 and 70, undergoing the dialysis therapy.

In the dosage of the renal failure progression inhibitor of the present embodiment, 3 to 15 g of paramylon or a processed product thereof per day may be orally administered to a patient with renal failure. In the oral administration, the dose is preferably 3 to 9 g per day, more preferably 6 g per day. Further, a prescribed amount of paramylon or the processed product thereof may be administered at once per day, but preferably administered in several divided doses per day, more preferably administered in three divided doses per day.

Further, the renal failure progression inhibitor may be continuously administered to a patient with renal failure, preferably for 9 weeks or more.

Further, a dosage form of the renal failure progression inhibitor is preferably a solid preparation such as a tablet, a granule, a capsule, a powdered preparation, and a powder, more preferably a capsule and a powdered preparation.

The renal failure progression inhibitor of the present embodiment may be administered to a patient with renal failure before or after meal.

Further, the renal failure progression inhibitor may be singly administered to a patient with renal failure instead of being administered concomitantly with other drug. The renal failure progression inhibitor is preferably administered at a prescribed time interval before and after the administration of other drugs.

As a comparison, a spherical adsorptive carbon representing a conventional renal failure progression inhibitor usually needs to be administered at 6 g per day (30 capsules provided that each capsule contains 200 mg of the drug or 3 envelopes in a granular provided that each envelope contains 2 g of the drug) in three divided doses. This dosage is significantly higher than that of a conventional pharmaceutical product and such a high dosage causes a feeling of sandy texture in the oral cavity even in a granular formulation, making the intake of the drug hard. Moreover, the spherical adsorptive carbon causes a side effect such as abdominal distension and constipation, putting a high burden on the patient.

In contrast to this, paramylon or the processed product thereof of the present invention can be administered at the same 6 g per day by taking 24 capsules, each capsule containing 250 mg of the drug, or envelopes of powdered preparations in three divided doses. The number of capsules to be administered is reduced and, even when the powdered preparations are used, they have a better texture in the mouth and do not cause a side effect such as abdominal distension and constipation. As a result, pains and burdens caused to the patient with renal failure can be reduced and the drug can be easily ingested by the patient for a long period of time.

<Therapeutic Agent for Renal Failure and Prophylactic Agent for Renal Failure>

In the present embodiment, the description is mainly given to the renal failure progression inhibitor. However, the present invention containing paramylon or the processed product thereof as an active ingredient may be also used as a therapeutic agent for renal failure, intended for a patient with renal failure and an animal other than human, suffering from renal failure.

The therapeutic agent for renal failure reduces the blood concentration of indoxyl sulfate in a living body to a normal range by virtue of paramylon administered to the living body.

Specifically, there can be provided the therapeutic agent for renal failure capable of synergistically increasing the inhibitory effect of renal failure progression, the therapeutic agent for renal failure being formulated by combining paramylon in an amount sufficient for effectively exhibiting effect of lowering the blood concentration of indoxyl sulfate with pharmaceutically acceptable carriers and additives.

Further, the present invention containing paramylon or the processed product thereof as an active ingredient may be also used as a prophylactic agent for renal failure, intended for a living organism, for example, human before affection to renal failure, human at risk of renal failure, and human before being diagnosed or treated with renal failure, and an animal other than human.

The prophylactic agent for renal failure controls the blood concentration of indoxyl sulfate in a living body to a normal range by virtue of paramylon administered to the living body.

<Indoxyl Sulfate Production Inhibitor and Other Therapeutic Agent and Prophylactic Agent>

The present invention containing paramylon or the processed product thereof as an active ingredient may be also used as an indoxyl sulfate production inhibitor that reduces the blood concentration of indoxyl sulfate produced in a living body.

The indoxyl sulfate production inhibitor can function as a progression inhibitor, a therapeutic agent, or a prophylactic agent of renal failure, as well as a therapeutic agent or a prophylactic agent for diseases associated with renal failure, such as nephritis (glomerulonephritis), nephropathy (diabetic nephropathy and IgA nephropathy), cardiovascular disease, heart failure, myocardial infarction, and apoplexy. Further, the present invention can also function as a prophylactic agent or a therapeutic agent for a disease which is alleviated by reduction of the blood concentration of indoxyl sulfate.

Further, the present invention can be used as a therapeutic agent for uremia, which is administered to a patient with uremia and a therapeutic agent for cardiovascular disease associated with chronic renal failure, which is administered to a patient with chronic kidney disease (CKD).

In addition, the present invention can be used as a prophylactic agent or a therapeutic agent for a disease associated with renal failure, such as nephritis (glomerulonephritis), nephropathy (diabetic nephropathy and IgA nephropathy), cardiovascular disease, heart failure, myocardial infarction, and apoplexy, and a supplementary agent used for fine adjustment of the physical condition after a treatment of these diseases.

EXAMPLE

Paramylon derived from *Euglena* was prepared (produced) by a following procedure.

*Euglena gracilis* powders (manufactured by *euglena* Co., Ltd.) were put into distilled water and stirred at room temperature for 2 days. The suspension solution was subjected to an ultrasonic treatment to break cell membranes and crude paramylon particles were recovered by centrifugal separation. Recovered paramylon particles were dispersed into a 1% dodecyl sodium sulfate aqueous solution and heated to 95° C. for 2 hours. Paramylon particles again recovered by centrifugal separation were dispersed into a 0.1% dodecyl sodium sulfate aqueous solution and heated to 50° C. for 30 min. Paramylon particles removed of lipids and proteins by the above operations were washed with acetone and ether, and dried at 50° C. to obtain purified paramylon particles.

Paramylon thus prepared was packed into a capsule known as a solid preparation to obtain a renal failure progression inhibitor.

Test Example 1

Administration Test of Renal Failure Progression Inhibitor to Patient with Chronic Renal Failure>

Human clinical trials were performed to study the inhibitory effect of renal failure progression using the renal failure progression inhibitor of Example.

Subjects of the present trials consisted of 48 patients with chronic renal failure (16 males and 32 females) between the ages of 40 and 88, currently undergoing a dialysis therapy. The average age of the subjects was 67.81 years old and the average dialysis treatment duration was 9.88 years.

The subjects were divided at random into a paramylon-treated group (29 subjects) to which the renal failure progression inhibitor was administered and a control group (19 subjects) to which no renal failure progression inhibitor was administered. The subjects in the paramylon-treated group were asked to orally ingest the renal failure progression inhibitor of Example alone between meals, daily, three times a day, in a dose of 2 g (8 capsules or powdered preparations) per intake. In particular, the oral ingestion was performed at a prescribed time interval before and after administration of other drugs. The oral ingestion was continued for 9 weeks.

It is noted that, among 29 subjects in the paramylon-treated group, 3 subjects dropped out because of the renal failure progression inhibitor (due to difficulty ingesting many capsules, etc.) and 4 subjects dropped out for other reasons. Further, 1 subject among 19 subjects in the control group dropped out for some reasons.

The blood was collected from each subject just before the start of ingestion of the renal failure progression inhibitor and 9 weeks after the start of ingestion. The blood concentration of indoxyl sulfate was measured using collected whole blood, and an amount of change of the blood concentration of indoxyl sulfate was monitored. Details of the measurement method are described as follows.

(1) Pretreatment of Samples

Ten µl of serum from each subject was added with trichloroacetic acid (4% TCA) and stirred. After centrifugal separation, a supernatant was collected in a sample vial for analysis to obtain a serum sample (the protein removal treatment). The serum sample was diluted 10 times by this treatment.

Ten µl of serum from a healthy person was added with a standard indoxyl sulfate stock solution at final concentrations of 0.0 (no adding) and 5.0 (µg/ml) and then subjected to the above-mentioned protein removal treatment to prepare external standard calibration curve samples 1 and 2.

(2) HPLC Quantitative Analysis Using External Standard Calibration Curve Method

Supernatants of the above standard samples 1 and 2 were taken in a volume of 2.5 µl and subjected to separation analysis using a high performance liquid chromatography (HPLC) device (L-2000 manufactured by Hitachi High-Technologies Corp.) to calculate concentrations (µg/ml) using an external standard calibration curve method.

(3) Sample Analysis

The above serum samples were analyzed in the prescribed sequence.

The external standard calibration curve was obtained by performing fitting of analysis results of the first and last two calibration curve samples 1 and 2 using a least squares method, and concentrations of indoxyl sulfate (µg/ml) in the serum samples were determined.

Final blood concentrations of indoxyl sulfate were obtained by multiplying analysis results of the serum samples by a dilution rate 10. It is noted that the serum sample of a healthy person was prepared as a blank and added in advance to the analysis results of the serum samples derived from the subjects.

Subjects' ages (years), dialysis treatment duration (years), gender, and the measurement results of the blood concentration of indoxyl sulfate (µg/ml) before and after the intake were compared between the control group and the paramylon-treated group.

FIG. 1 shows a graph comparing an average change amount (average reduction amount) of the blood concentration of indoxyl sulfate before and after the intake between the control group (22 subjects) and the paramylon-treated group (18 subjects), obtained by analyzing the above measurement results.

Figure 2:
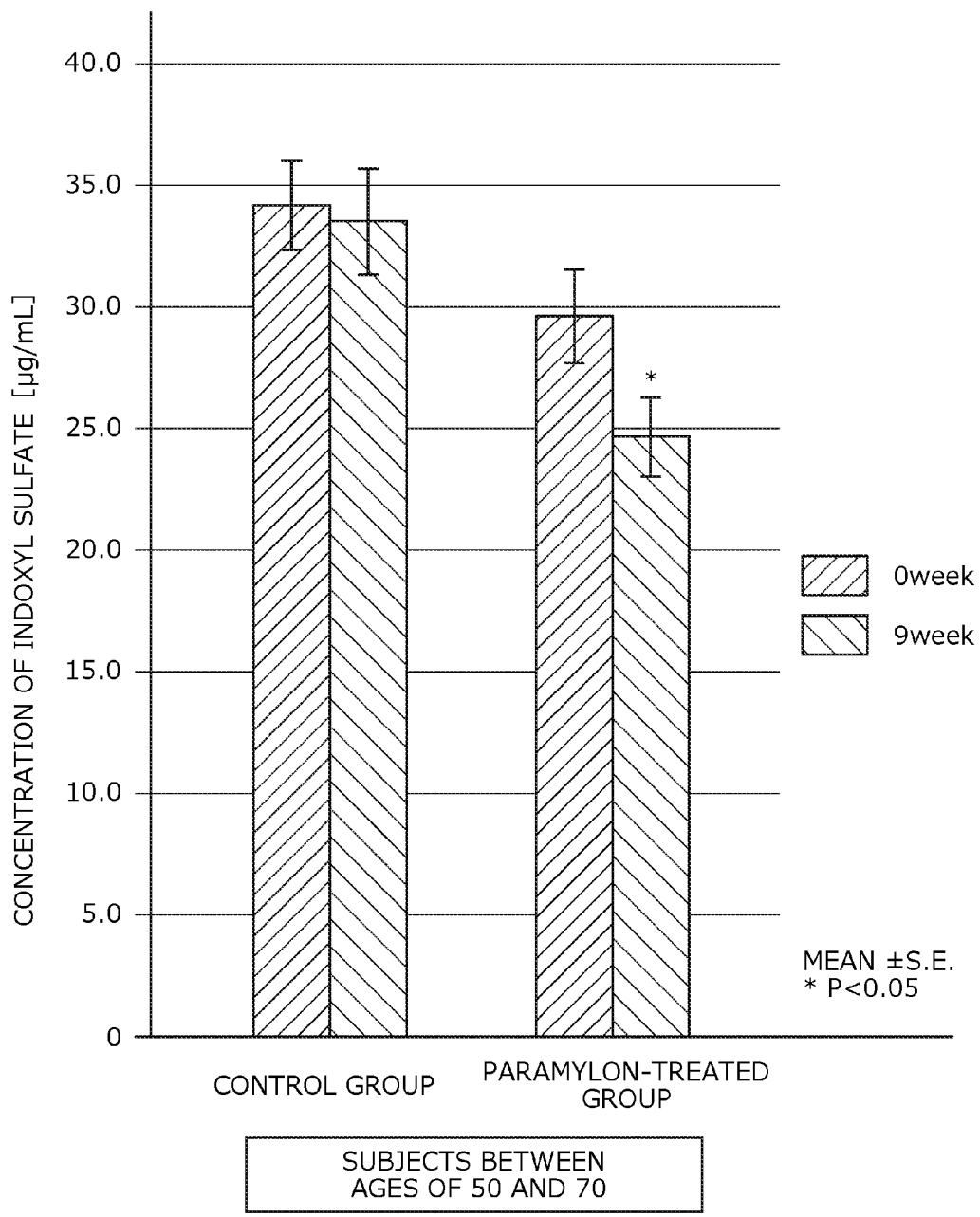
FIG. 2 is a graph illustrating an amount of change of the blood concentration of indoxyl sulfate in a patient with renal failure between the ages of 50 and 70, who receives the renal failure progression inhibitor for 9 weeks.

Further, FIG. 2 shows a graph comparing an average change amount (average reduction amount) of the blood concentration of indoxyl sulfate before and after the intake between the control group (8 subjects) and the paramylon-treated group (10 subjects), obtained by limiting the subjects to those between the ages of 50 and 70 (18 subjects).

Figure 3:
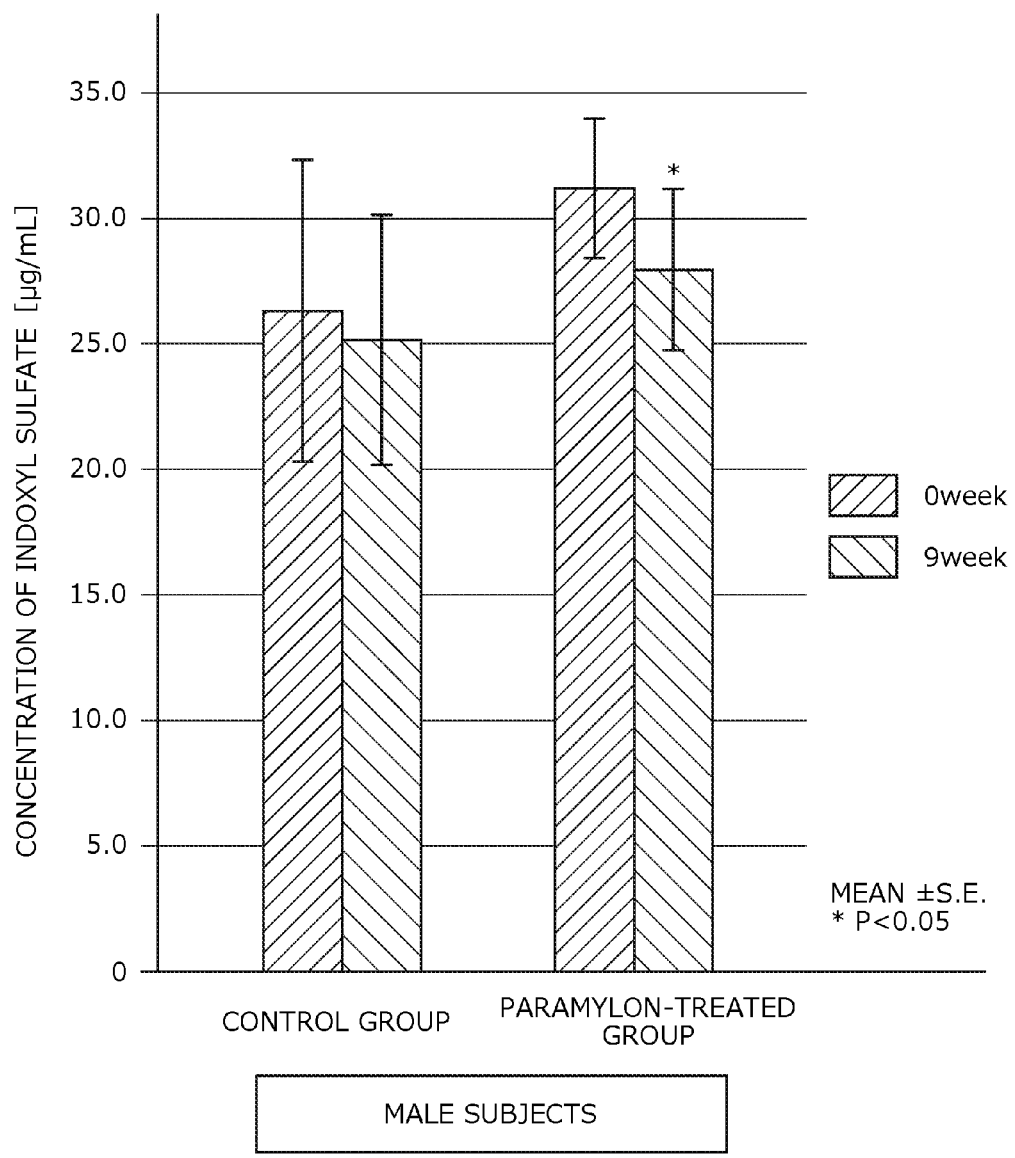
FIG. 3 is a graph illustrating an amount of change of the blood concentration of indoxyl sulfate in a male patient with renal failure, who receives the renal failure progression inhibitor for 9 weeks.

Further, FIG. 3 shows a graph comparing an average change amount (average reduction amount) of the blood concentration of indoxyl sulfate before and after the intake between the control group (6 subjects) and the paramylon-treated group (16 subjects), obtained by limiting the subjects to males (22 subjects).

As is apparent from FIG. 1, the blood concentrations of indoxyl sulfate of all available patients in the paramylon-treated group were significantly reduced (P<0.05 determined by t-test) during a nine-week administration period. On the other hand, the blood concentrations of indoxyl sulfate of all available patients in the control group did not significantly change.

Further, as is apparent from FIG. 2, the blood concentrations of indoxyl sulfate of the patients between the ages of 50 and 70 in the paramylon-treated group were significantly reduced (P<0.05 determined by t-test). On the other hand, the blood concentrations of indoxyl sulfate of the patients in the control group did not significantly change.

Further, as is apparent from FIG. 3, the blood concentrations of indoxyl sulfate of the male patients in the paramylon-treated group were significantly reduced (P<0.05 determined by t-test). On the other hand, the blood concentrations of indoxyl sulfate of the patients in the control group did not significantly change.

Discussion on Test Example 1

Based on the results of Test Example 1, the blood concentrations of indoxyl sulfate were significantly reduced in the patients with chronic renal failure between the ages of 40 and 88, currently undergoing a dialysis therapy, by continuous administration of the renal failure progression inhibitor of Example for 9 weeks.

In particular, the blood concentrations of indoxyl sulfate were significantly reduced in such patients who orally ingested the renal failure progression inhibitor alone between meals, daily, three times a day, in a dose of 2 g (8 capsules or powdered preparations) per intake, and at a prescribed time interval before and after administration of other drugs.

Further, the blood concentrations of indoxyl sulfate were significantly reduced especially in the patients between the ages of 50 and 70, among all patients with chronic renal failure between the ages of 40 and 88 undergoing a dialysis therapy, by administration of the renal failure progression inhibitor.

Further, the blood concentrations of indoxyl sulfate were significantly reduced especially in the male patients, among all patients with chronic renal failure between the ages of 40 and 88 undergoing a dialysis therapy, by administration of the renal failure progression inhibitor.

Further, in general, when patients with renal failure are asked to continuously ingest a conventional spherical adsorptive carbon, around half of the patients often drop out due to, for example, difficulty in ingestion and a strong side effect such as abdominal distension and constipation. In contrast, when patients were asked to continuously ingest the renal failure progression inhibitor, only 3 patients among 29 patients in the paramylon-treated group dropped out because of the renal failure progression inhibitor.

According to impressions of the subjects obtained by actual medical inquiry conducted by a medical doctor, the renal failure progression inhibitor was readily ingested as compared with the conventional spherical adsorptive carbon and did not cause abdominal distension, further, symptoms such as constipation were ameliorated.

Moreover, the present Test Example 1 was performed without informing the subjects of the effect of the renal failure progression inhibitor. Regarding this point, the medical doctor concluded as a diagnostic result that the less patients would have dropped out if the subjects were informed in advance of the effect of the renal failure progression inhibitor.

In particular, a patient with renal failure undergoing a dialysis therapy is, in general, likely to become constipated due to limitation on water intake. Regarding this point, the medical doctor concluded as a diagnostic result that the less patients would have dropped out if the patients (subjects) were informed in advance of the effect of improving an intestinal environment, one of the effects exhibited by the renal failure progression inhibitor, since such an effect caused the effect of ameliorating constipation, which was not exhibited by the conventional spherical adsorptive carbon.

Thus, it was found that the renal failure progression inhibitor of Example could suppress the progression of renal failure of the patient with chronic renal failure undergoing the dialysis therapy by reducing the blood concentration of indoxyl sulfate in the living body.

Further, it was found that, as compared with the spherical adsorptive carbon representing the conventional renal failure progression inhibitor, the renal failure progression inhibitor was readily ingested and hardly caused a side effect such as abdominal distension and constipation, allowing the patient with chronic renal failure to readily orally ingest the renal failure progression inhibitor for a long period of time.

Test Example 2

Indole Adsorption Performance Test

A test was performed to verify indole adsorption performance of paramylon prepared in Example.

Details of the method are described as follows.

(1) Preparation of Calibration Curve

Indole solutions at concentrations of 0, 10, 20, 30, 40, and 50 ng/ml were prepared and their absorbance at an excitation wavelength of 342 nm was measured using a fluorescence spectrophotometer (F-2500 manufactured by Hitachi High-Technologies Corp.) to prepare a calibration curve showing a relationship between indole concentrations and absorbance.

(2) Measurement of Residual Concentration of Indole after Mixing Paramylon

To an indole solution at a concentration of 30 ng/ml, paramylon was added to 2 vol %, and the mixture was mixed for 1 min using a vortex mixer. Paramylon was then spun down at a rotation speed of 6,200 rpm for 1 min using a centrifuge and a supernatant was recovered as a sample.

Specifically, the following 5 samples were prepared and their absorbance at an excitation wavelength of 342 nm was measured using the fluorescence spectrophotometer. Sample 1: supernatant was recovered by centrifuge right after mixing, Sample 2: supernatant was recovered by centrifuge after mixture was mixed and allowed to stand for 10 min, Sample 3: supernatant was recovered by centrifuge after mixture was mixed and allowed to stand for 30 min, Sample 4: supernatant was recovered by centrifuge after mixture was mixed and allowed to stand for 60 min, Sample 5: supernatant was recovered by centrifuge after mixture was mixed and allowed to stand for 1,440 min (24 hours).

On the other hand, paramylon was added to purified water to 2 vol % and the mixture was mixed for 1 min in the same manner. After paramylon was spun down by a centrifuge, a supernatant was recovered as a blank solution. Absorbance of the blank solution was measured at an excitation wavelength of 342 nm.

A residual concentration of indole in the indole solution was calculated by subtracting an absorbance value measured in the blank solution from an absorbance value measured in each of the samples 1 to 5. The calculation result verified a change over time of indole adsorption performance of paramylon.

Figure 4:
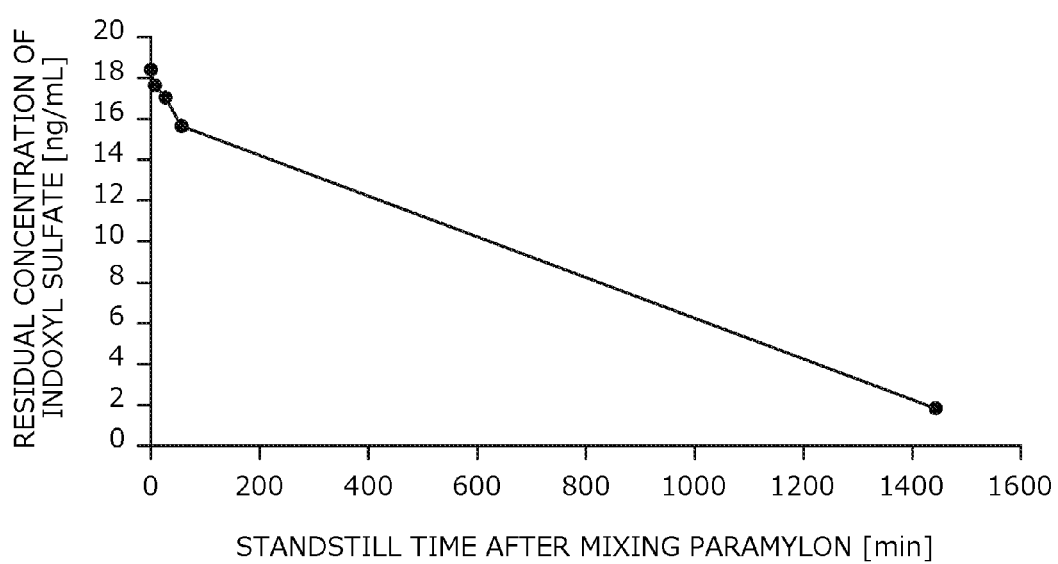
FIG. 4 is a graph illustrating a change over time of a residual concentration of indole in a solution after mixing paramylon of this example into an indole solution.

As a test result, FIG. 4 shows a graph illustrating a relationship between standstill time after mixing paramylon and residual concentrations of indole.

As is apparent from FIG. 4, it was found that the residual concentration of indole in the indole solution was reduced by mixing paramylon into the indole solution.

Further, it was found that the residual concentration of indole in the indole solution became lower with an increase in the standstill time after mixing paramylon into the indole solution.

Discussion on Test Example 2

Based on the results of Test Example 2, it was found that indole contained in the indole solution was absorbed by paramylon when paramylon was mixed into the indole solution.

Further, it was found that an adsorption amount of indole by paramylon became higher with an increase in the standstill time after mixing paramylon into the indole solution.

Thus, it was found that paramylon of Example was effective in absorbing indole in the intestine of human, in particular, a patient with renal failure.

Further, it was found that an absolute amount of indole, a precursor of indoxyl sulfate, was reduced, thus the release of indoxyl sulfate into the blood could be suppressed and the blood concentration of indoxyl sulfate could be reduced.

Test Example 3

Verification Test of Intestinal Good Bacteria Proliferation

A test was performed to verify the effect of paramylon in improving an intestinal environment by feeding paramylon prepared in Example to a rat. Specifically, in this test, the occupancy of good bacteria in the intestinal bacterial flora was measured.

In the test, fifteen male rats of the Wistar strain (CLEA Japan), 3 weeks of age, were used. Feed and drinking water (distilled water) were provided ad lib.

After one-week preliminary breeding, the rats were divided into three groups each including five rats, followed by another four-week bleeding. A feed was prepared based on a purified diet (AIN-93N; CLEA Japan). A feed without cellulose was fed to a control group. Further, a feed containing 5% cellulose was fed to a cellulose-treated group, while a feed containing 5% paramylon prepared in Example, instead of cellulose, was fed to a paramylon-treated group (see feed composition in Table 1 below).

TABLE 1

| Ingredient (%) | Feed | | |
|---|---|---|---|
| | Control group | Cellulose-treated group | Paramylon-treated group |
| L-Cystine | 0.2 | 0.2 | 0.2 |
| Mineral mix | 3.7 | 3.5 | 3.5 |
| Milk casein | 14.8 | 14.0 | 14.0 |
| Vitamin mix | 1.1 | 1.0 | 1.0 |
| Soybean oil | 4.2 | 4.0 | 4.0 |
| β-Cornstarch | 49.1 | 46.6 | 46.6 |
| α-Cornstarch | 16.4 | 15.5 | 15.5 |
| Granulated sucrose | 10.6 | 10.0 | 10.0 |
| Tert-butylhydroquinone | 0.0008 | 0.0008 | 0.0008 |
| Cellulose | — | 5.0 | — |
| Paramylon | — | — | 5.0 |
| Total | 100 | 100 | 100 |

*Total values were rounded to obtain 100.

In the test, the occupancy in the intestinal bacterial flora of genus *Lactobacillus* and genus *Bifidobacterium*, classified into good bacteria, genus *Clostridium* classified into bad bacteria, and genus *Prevotella* and genus *Bacteroides*, classified into opportunistic bacteria, was measured in the rats of each group. Further, a ratio between good bacteria and bad bacteria was measured.

Specifically, analysis of nucleotide sequence of a part of 16S rRNA derived from the bacterial flora was performed based on a known method to determine the intestinal bacterial flora of the cecum in each rat (Nagashima K, et al. (2003) "Application of New Primer-Enzyme Combinations to Terminal Restriction Fragment Length Polymorphism Profiling of Bacterial Populations in Human Feces" Appl Environ Microbiol, 69, 1251-1262).

Figure 5:
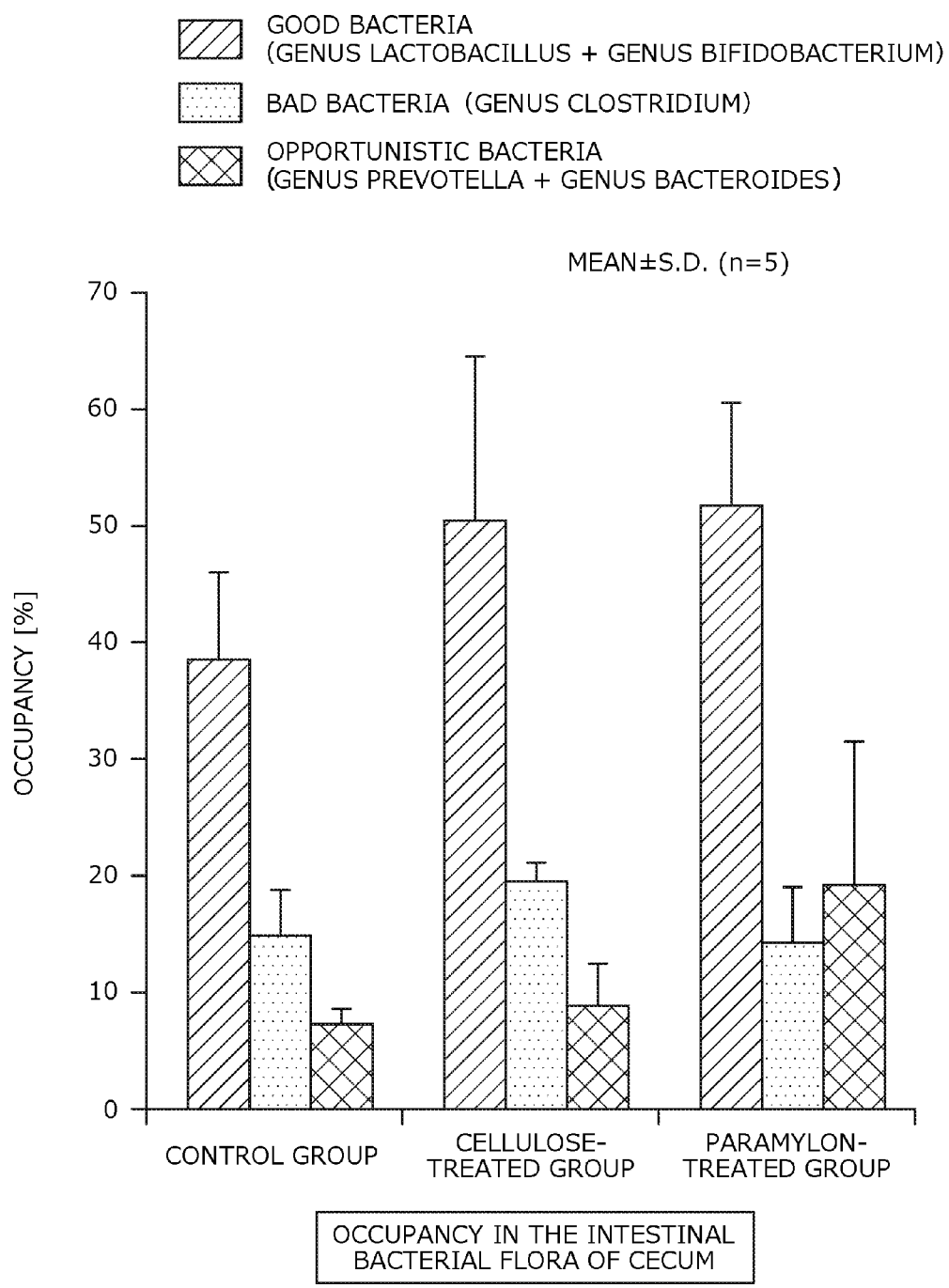
FIG. 5 is a graph comparing the occupancy in the intestinal bacterial flora of the cecum in a rat, which receives paramylon of the example of the present invention for 4 weeks.

As a test result, FIG. 5 shows a graph comparing the occupancy in the intestinal bacterial flora of the cecum between the control group, the cellulose-treated group, and the paramylon-treated group. Further, FIG. 6 shows a graph comparing the ratio of good bacteria/bad bacteria in the cecum.

As is apparent from FIG. 5, the occupancy of good bacteria was higher in the paramylon-treated group and the cellulose-treated group as compared with the control group. A significant difference in the occupancy of bad bacteria was not observed between three groups. The occupancy of opportunistic bacteria was higher in the paramylon-treated group as compared with the other two groups.

Figure 6:
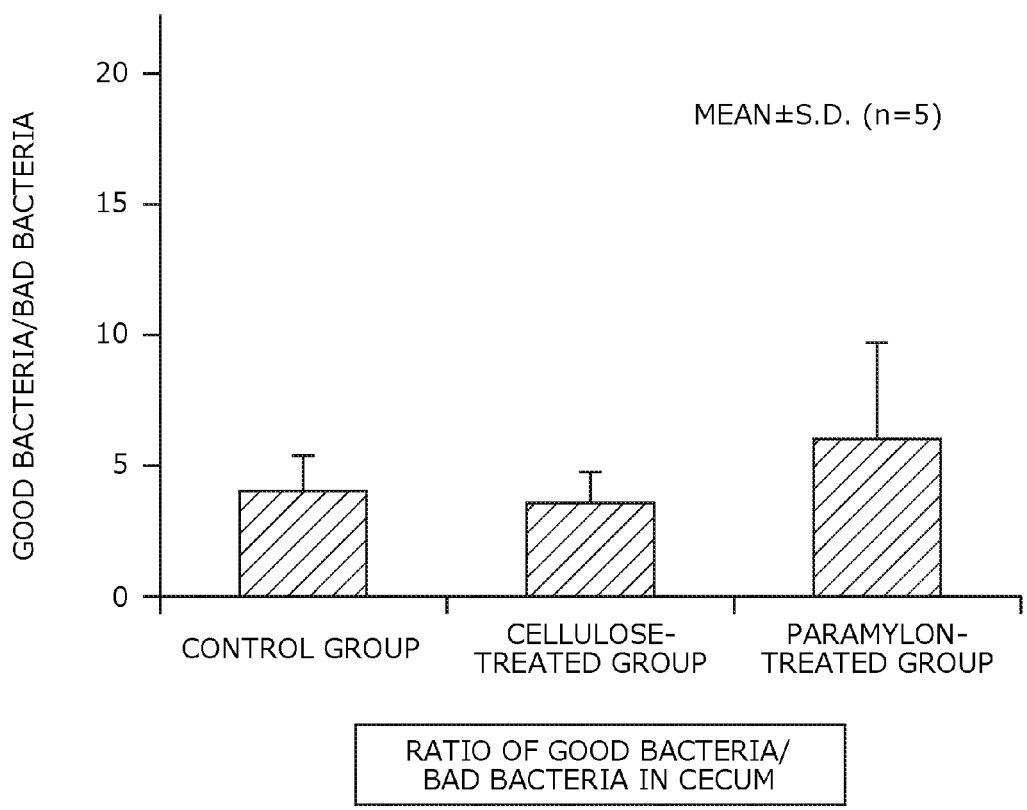
FIG. 6 is a graph comparing a ratio of good bacteria/bad bacteria in the cecum shown in FIG. 5.

Further, as is apparent from FIG. 6, the ratio of good bacteria and bad bacteria was higher in the paramylon-treated group as compared with the other two groups.

Discussion on Test Example 3

Based on the results of Test Example 3, the occupancy of good bacteria in the intestinal bacterial flora was higher in the paramylon-treated group and the cellulose-treated group, where the rats were continuously fed with paramylon and cellulose, both being insoluble dietary fiber, respectively. Further, the ratio of good bacteria and bad bacteria in the intestinal bacterial flora was higher in the rats of the paramylon-treated group as compared with the other two groups.

In another words, paramylon had the effect of improving an intestinal environment. Indeed, paramylon had the effect of improving an intestinal environment equal to or greater than that of cellulose.

Thus, it was found that paramylon orally administered to a living body activates and propagates good bacteria including bifidobacteria and lactic acid bacteria in the intestine, thereby improving the balance of the intestinal bacteria.

As a result, it was found that suppressing the growth of intestinal bad bacteria could suppress the production amount of indole, produced by the decomposition of tryptophan contained in proteins of the diet by intestinal bad bacteria, thus, the production amount of indoxyl sulfate could be suppressed.

In particular, it was found that, while a conventional spherical adsorptive carbon could not be administered to a patient with renal failure accompanied by digestive tract obstruction due to a possibility of causing a trouble in excretion, paramylon of the present invention could be administered to such a patient without causing a trouble in excretion.

Test Example 4

Measuring Test of Intestinal Transit Time of Orally Ingested Diet

A test was performed to verify the effect of paramylon in improving an intestinal environment by feeding paramylon prepared in Example to a rat. Specifically, this test was performed to measure the intestinal transit time of paramylon-containing feed that was fed.

In the test, as in Test Example 2, fifteen male rats of the Wistar strain, 3 weeks of age, were used. Feed and drinking water (distilled water) were provided ad lib.

After one-week preliminary breeding, the rats were divided into three groups each including five rats, followed by another four-week bleeding. A feed without cellulose was fed to a control group. Further, a feed containing 5% cellulose was fed to a cellulose-treated group, while a feed containing 5% paramylon prepared in Example, instead of cellulose, was fed to a paramylon-treated group (see feed composition in Table 1 above).

In the test, a feed containing 5% carmine dye was fed at 18 o'clock in the second week (13th day) and the fourth week (27th day) after the start of the bleeding, and the time until the first appearance of red feces was measured. The appearance was checked hourly from 0 o'clock to 3 o'clock, then every thirty minutes after 3 o'clock.

During the breeding period, the rats were fasted between 9 o'clock to 18 o'clock in the second week and the fourth week for the purpose of measuring the intestinal transit time. Feed was provided ad lib for the other period of time.

Figure 7:
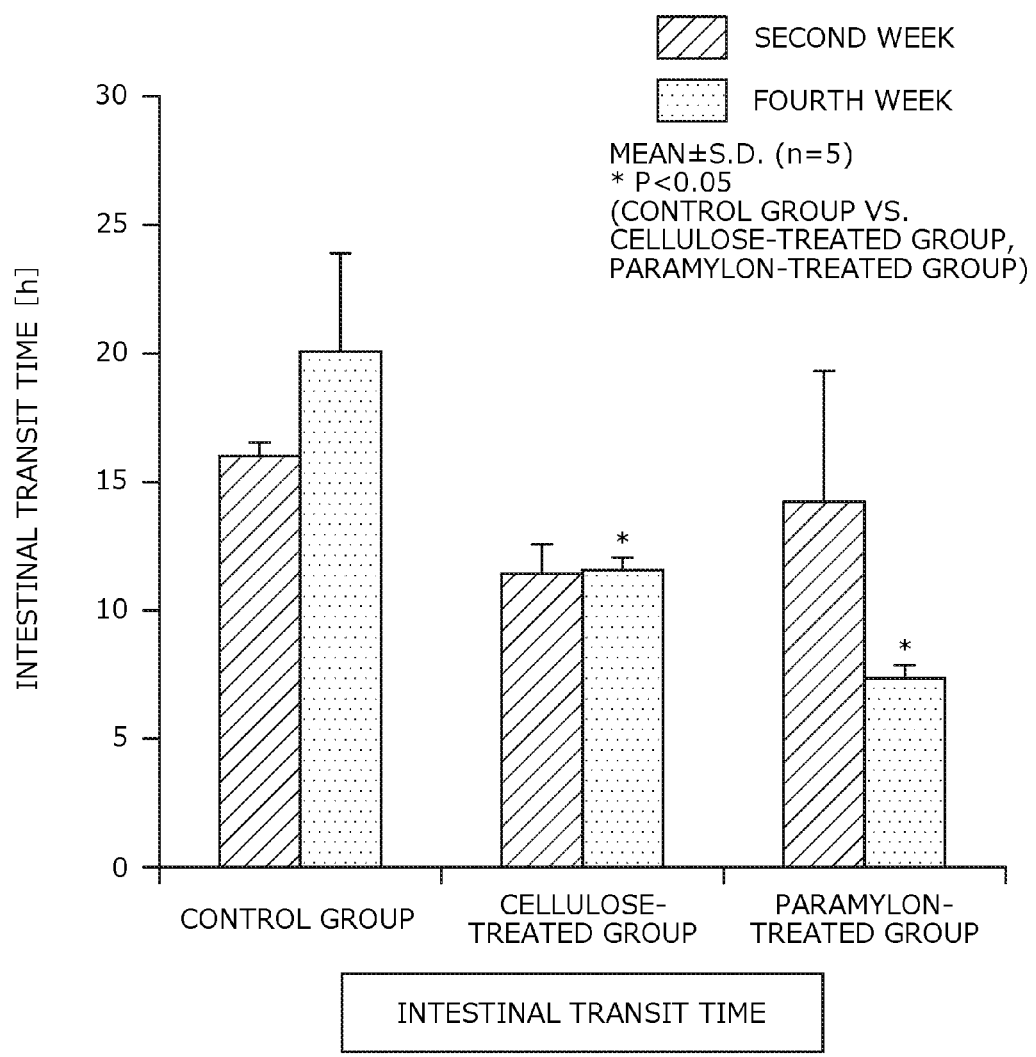
FIG. 7 is a graph comparing intestinal transit time in a rat, which receives paramylon of this example for 4 weeks, the intestinal transit time being measured in the second week and the fourth week after the start of the bleeding.

As a test result, FIG. 7 shows a graph comparing the intestinal transit time in the second week and the fourth week after the start of the bleeding between the control group, the cellulose-treated group, and the paramylon-treated group.

As is apparent from FIG. 7, a significant difference was not observed in the intestinal transit time measured in the second week between the control group, the cellulose-treated group, and the paramylon-treated group.

The intestinal transit time measured in the fourth week was shortest in the paramylon-treated group. The intestinal transit time in the paramylon-treated group and the cellulose-treated group was significantly shorter than that in the control group. There was no significant difference in the intestinal transit time between the paramylon-treated group and the cellulose-treated group.

Discussion on Test Example 4

Based on the results of Test Example 4, it was observed that the intestinal transit time in the rats to which paramylon was continuously administered for 4 weeks was shorter as compared to the control group.

Further, it was observed that continuous administration of paramylon and cellulose equally shortened the intestinal transit time. In other words, it was found that paramylon had the effect of improving an intestinal environment equal to that of cellulose.

Thus, it was found that oral administration of paramylon to a living body shortened the intestinal transit time of the diet that was orally ingested.

As a result, it was found that the production amount of indole, produced from tryptophan while the diet passed through the intestine, was suppressed, thus the production amount of indoxyl sulfate was suppressed.

Test Example 5

Measuring Test of Fecal Weight

A test was performed to verify the effect of paramylon in improving an intestinal environment by feeding paramylon prepared in Example to a rat. Specifically, this test was performed to measure weight of feces excreted from the rat fed with paramylon.

In the test, as in Test Examples 2 and 3, fifteen male rats of the Wistar strain, 3 weeks of age, were used. Feed and drinking water (distilled water) were provided ad lib.

After one-week preliminary breeding, the rats were divided into three groups, namely, the control group, the cellulose-treated group, and the paramylon-treated group, each including five rats, followed by another four-week breeding.

In the test, feces were collected for 3 days (from 11th to 13th days) in the second week after the start of the breeding and again for 3 days (from 25th to 27th days) in the fourth week after the start of the breeding, before slaughter. The collected feces were measured for their dry weight and water content. It is noted that the water content of feces was measured after feces were dried at 100° C. for 24 hours.

Figure 8:
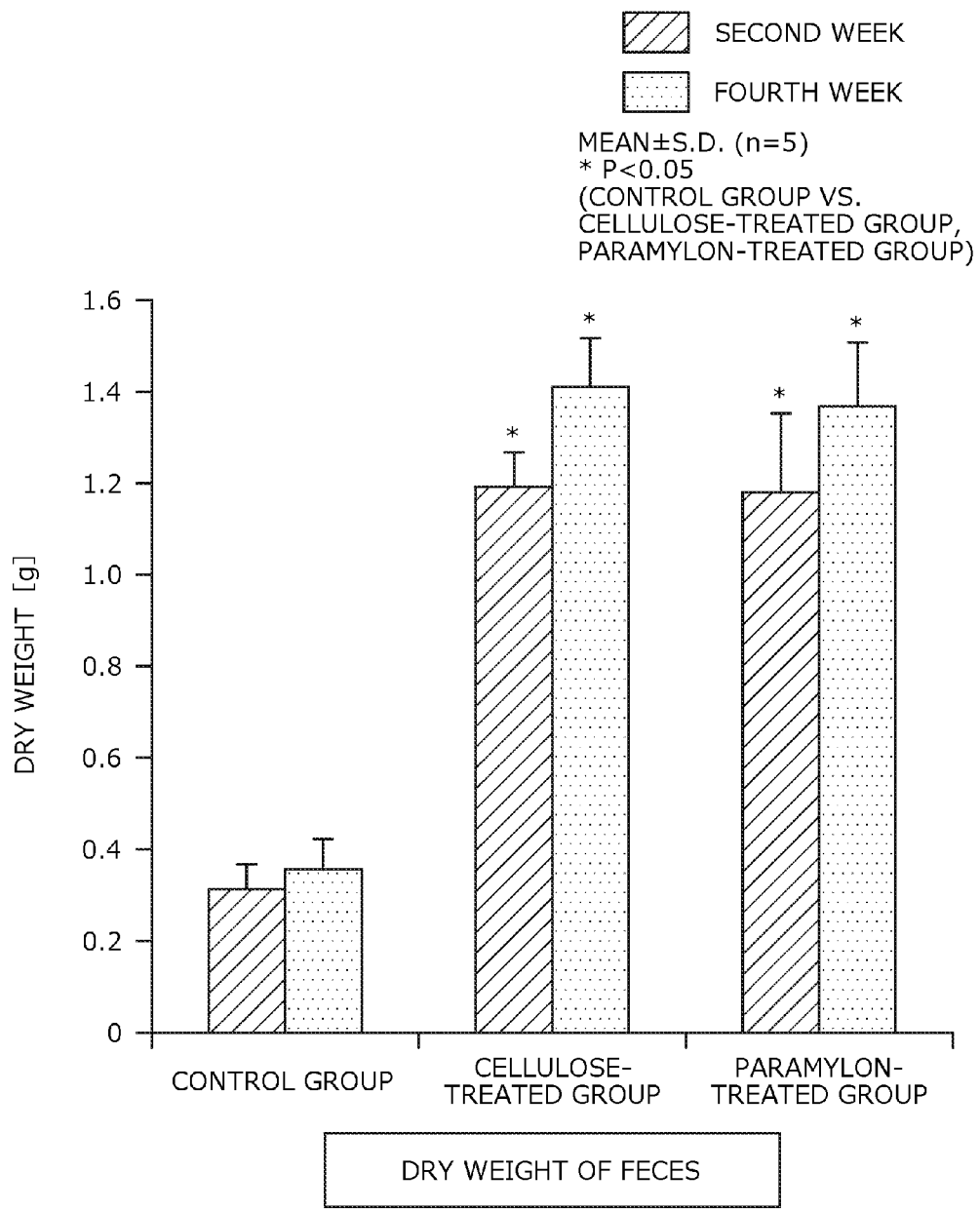
FIG. 8 is a graph comparing weight of feces in a rat, which receives paramylon of this example for 4 weeks, the weight of feces being measured in the second week and the fourth week after the start of the bleeding.
Figure 9:
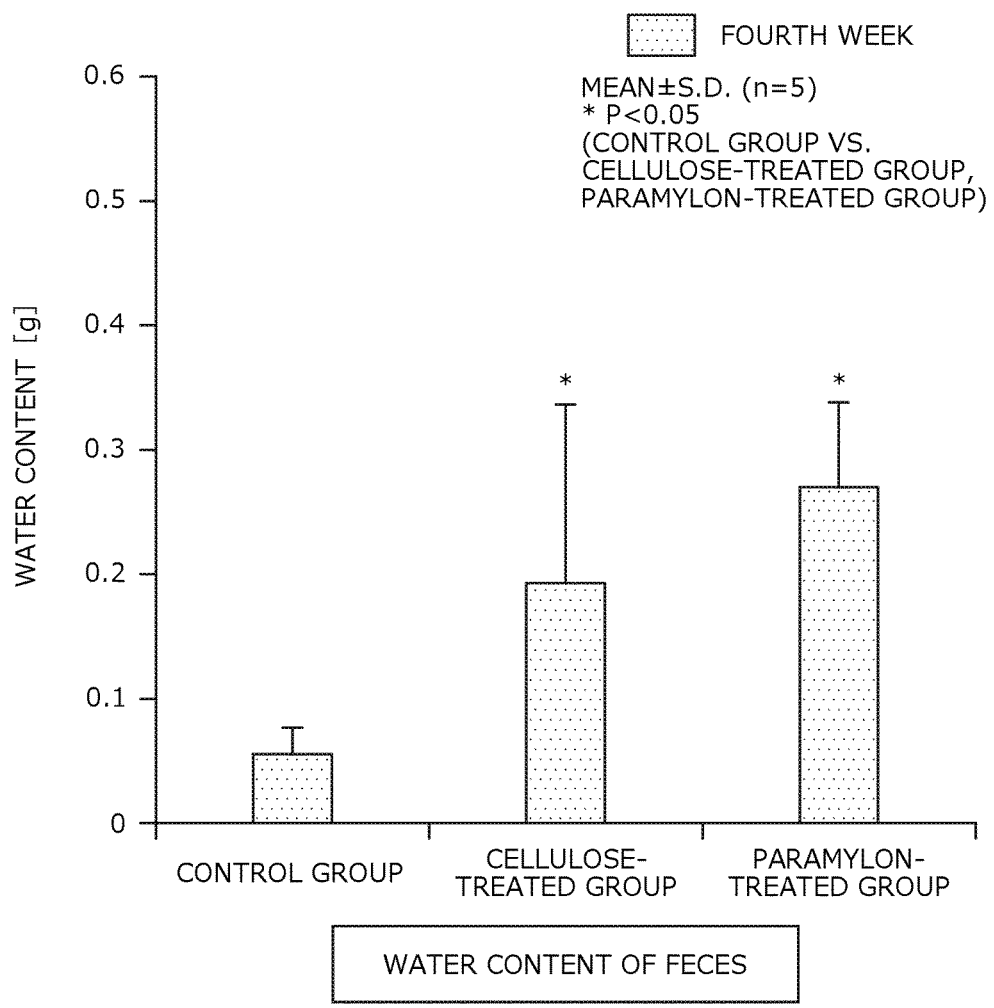
FIG. 9 is a graph comparing water content of feces in the rat shown in FIG. 8, the water content being measured in the second week and the fourth week after the start of the bleeding.

As a test result, FIG. 8 and FIG. 9 respectively show graphs comparing weight and water content of feces in the second week and the fourth week after the start of the breeding between the control group, the cellulose-treated group, and the paramylon-treated group.

As is apparent from FIG. 8, weight of feces measured in the second week and the fourth week was significantly higher in the paramylon-treated group and the cellulose-treated group than that in the control group (P<0.05 determined by t-test). There was no significant difference between the paramylon-treated group and the cellulose-treated group.

As is apparent from FIG. 9, water content of feces measured in the fourth week was significantly higher in the paramylon-treated group as compared to the control group, and it was also higher in the paramylon-treated group as compared to the cellulose-treated group (P<0.05 determined by t-test).

Discussion on Test Example 5

Based on the results of Test Example 5, it was observed that weight and water content of feces excreted from the rats to which paramylon was continuously administered for 4 weeks increased as compared to the control group.

Further, it was observed that continuous administration of paramylon and cellulose equally increased weight of feces.

In another words, it was found that paramylon had the effect of improving an intestinal environment equal to that of cellulose.

Thus, it was found that oral administration of paramylon to a living body increased weight and water content of feces after oral administration.

It has been reported that, in general, when fecal weight increases and water retentivity of feces increases, the intestinal transit time of the diet is shortened (Keiko Oikawa, Effect of so-called dietary fiber drink on fecal weight and intestinal transit time in a rat, as well as a bowel movement in human, Annual report of the Faculty of Education, University of Iwate, 55, 111-118 (1995)).

Therefore, it was found that the production amount of indole, produced from tryptophan while the diet passed through the intestine, was suppressed, thus the production amount of indoxyl sulfate was suppressed.

The invention claimed is:

1. A method for inhibiting indoxyl sulfate production in a patient, comprising:
    administering a composition comprising paramylon to a patient in need thereof.

2. A method for the treatment or prophylaxis of uremia, comprising:
    administering a composition comprising paramylon to a patient in need thereof.

* * * * *